United States Patent
Heidmann et al.

(10) Patent No.: US 9,797,855 B2
(45) Date of Patent: Oct. 24, 2017

(54) METHOD FOR DETERMINATION OF POLLEN VIABILITY AND/OR MATURATION GRADE OF A POLLEN POPULATION

(71) Applicant: Amphasys AG, Root Laengenbold (CH)

(72) Inventors: Iris Heidmann, Enkhuizen (NL); Marco Di Berardino, Rain (CH); Kim Kok, CC Volendam (NL); Grit Schade-Kampmann, Muehlau (CH)

(73) Assignee: Amphasys AG, Root Laengenbold (CH)

( * ) Notice: Subject to any disclaimer, the term of this patent is extended or adjusted under 35 U.S.C. 154(b) by 35 days.

(21) Appl. No.: 14/611,203

(22) Filed: Jan. 31, 2015

(65) Prior Publication Data

US 2015/0253273 A1 Sep. 10, 2015

(30) Foreign Application Priority Data

Mar. 6, 2014 (EP) .................................... 14158150

(51) Int. Cl.
| | | |
|---|---|---|
| *G01N 27/20* | (2006.01) | |
| *G01N 33/483* | (2006.01) | |
| *A01H 1/02* | (2006.01) | |
| *A01H 1/04* | (2006.01) | |

(52) U.S. Cl.
CPC ............. *G01N 27/20* (2013.01); *A01H 1/025* (2013.01); *A01H 1/04* (2013.01); *G01N 33/4833* (2013.01)

(58) Field of Classification Search
None
See application file for complete search history.

(56) References Cited

U.S. PATENT DOCUMENTS

2003/0102854 A1*  6/2003  Gascoyne .......... G01N 15/1218
                                          324/71.4

FOREIGN PATENT DOCUMENTS

WO    WO2012/129199 A2    9/2012

OTHER PUBLICATIONS

Detection and counting of micro-scale particles and pollen using a multi-aperture coulter counter; micro particle and pollen counting using a multi-aperture coulter counter, Jul. 1, 2006, Ashish V Jagtiani et al.
Microfluidic impedance-based flow cytometry, Jul. 1, 2010, Karen C. Cheung et al.
Impedance Flow Cytometry, Jul. 13, 2014, Di Berardino.

* cited by examiner

*Primary Examiner* — Suzanne M Noakes
*Assistant Examiner* — Stephen Chong
(74) *Attorney, Agent, or Firm* — Von Rohrscheidt Patents (57) ABSTRACT

A method for the determination of pollen viability and/or maturation grade of a pollen population, comprising mechanically removing pollen grains from flowers; re-suspending pollen grains in an electrically conductive buffer for keeping the plant cells to remain viable; passing the pollen suspension through an appropriate filter with a pore size suitable for a microfluidic device being adapted to perform impedance flow cytometry (IFC); An advantage of the present invention is that a plant cell does not have to be stained for viability analysis, the method is non-invasive and a high number of cells can be analyzed in a short time frame in real-time and on-site. It is possible to follow developmental processes of plant cells, and that it is applicable to all plant species. In particular, the method allows a standardized measurement independent of the location and all over the world.

11 Claims, 7 Drawing Sheets

METHOD FOR DETERMINATION OF POLLEN VIABILITY AND/OR MATURATION GRADE OF A POLLEN POPULATION

RELATED APPLICATIONS

This application claims priority from European patent application EP 14 158 150.4, filed on Dec. 19, 2014 which is incorporated in its entirety by this reference.

FIELD OF THE INVENTION

The present invention concerns a method for the determination of pollen viability and/or maturation grade of a pollen population and the use of a microfluidic device comprising at least one specific microfluidic chip and being adapted to perform impedance flow cytometry (IFC) with alternate current (AC).

BACKGROUND OF THE INVENTION

Analysis of cell viability, especially the one of pollen grains, plays an important role at various aspects of plant breeding and plant production processes via seeds.

Analysis of the viability of unripe pollen grains (microspores) is important for the production of homozygous parental lines and for the development of the specific protocols or methods thereof. The production of parental lines from pollen grains safes numerous generations in the breeding cycle and is therefore considered as essential for efficient parental line production. However, for an optimal production of these lines their donor plants have to be grown under optimal conditions.

The analysis of pollen quality plays an important role during the selection of male-sterile mother lines. The use of male-sterile maternal lines, based on cytoplasmic male sterility, which is only inherited by the female, are preferred not only in insect and wind pollinated species but also in hand-pollinated ones. Because of the missing pollen, male sterile maternal lines are unable to self-pollinate, which prevents the contamination of F1 seeds with maternal material, and have the advantage that labour-intensive emasculation steps can be omitted.

High quality pollen is essential for an efficient F1 hybrid seed production. High pollen quality will give maximum seed set whereas lower qualities will result in a lower yield and therefore lead to higher production costs per seed. Pollen quality is affected by its genetic constitutions, growth conditions of the plants but also by pesticides. It is common practise to apply pesticides before and during production processes to keep the fruit-bearing plants healthy as it can take to up to 2 months before fruits and seeds, respectively, can be harvested. Therefore, the viability of pollen should be monitored continuously during seed production, to indicate/predict and control the production, to estimate the optimal time point of pollination, e.g. after pesticide application or to test, which pesticides are not suitable, or to check the effect of other chemicals (e.g. fertilizers), or growth conditions, respectively.

Another common practise in breeding and F1 hybrid seed production as well as in germplasm preservation programs is to work with stored pollen. For any storage program the highest quality pollen should be used. Routine pollen viability analysis in this field will allow the optimization of storage protocols and subsequent processes.

Currently, no efficient, high-throughput and easily applicable technique exists to analyse pollen quality on-site.

Pollen viability is generally determined by various classical methods like staining techniques or in vitro germination assays. However, the results from various staining techniques do not always correlate with the in vitro germination and it cannot be applied to all species. The staining techniques are based on enzymatic reactions that might not be present in the pollen of all plant species, and in vitro pollen germination depends highly on the correct conditions, which need to be adjusted individually. Both, the current methods analysing pollen viability and germination are limited in the number of cells that can be analysed in a certain time frame and they are time consuming in preparation and analysis.

Furthermore, the current techniques require next to specific chemicals various specific equipment like fluorescent microscopes, incubators, and a person skilled in the art. In general, this means that these analyses are performed in analytical laboratories and cannot be performed "on-site" between the plants in a greenhouse or open field. Finally, since these analyses are quite complex to perform and involve several error-prone steps from sample preparation to analysis, their reproducibility can vary tremendously at different locations spanning the whole seed production process, i.e. the different sites where these data are urgently needed. Thus, experience shows that pollen viability data obtained at different geographical locations and even in closely related analytical laboratories are not always comparable and suffer from subjective errors.

The need of reliable apparatuses and methods for evaluating the quality of pollen and plants is widely recognised. WO 2012/129199 A2 discloses such methods for the discrimination and sorting of pollen and the determination of pollen viability. For these analyses either conventional fluorescence-based flow cytometers or optical density measurements are required. For fluorescence-based analyses the presence/absence of genetic markers are mandatory in order to permit discrimination when specific dyes bind to the respective cells. Even though this technique provides statistical data, it is not suitable for on-site analyses and works only if such genetic markers are available. The optical density measurements, on the other hand, provides a means for discriminating lysing pollen, but could deliver confusing data if pollen cells are in different developmental stages with potentially varying optical densities but still viable characteristics. In this regard, WO 2012/129199 A2 refrains from disclosing supporting data.

An "on-site" analysis of e.g. pollen cells that are going to be used in F1 hybrid seed production is of huge commercial interest with respect to saving production and subsequent costs. In the case of low quality (low viability) pollen it can be decided not to use it for pollination, reducing the subsequent efforts of pollen storage procedures, mass hand pollinations, growing the material until fruit harvest, seed extraction and further processing. An "on-site" analysis of pollen of breeding material would allow the easy and direct selection on male-fertile/male sterile, heat- and/or salt-tolerant plants making the selection process more efficient as well as reducing the labour of growing and maintaining the selected individual plants.

Not only seed production, but also fruit production relies on fertilization of the flowers with good quality pollen. The unknown effects of pesticides on the one hand, as well as the need of mass hand pollinations on the other hand (for example because of the extinction the respective insects) are calling for a simple tool to determine the pollen quality.

BRIEF SUMMARY OF THE INVENTION

Therefore, the problem to be solved of the present invention is to overcome the drawbacks of the prior art and to propose a simple and fast method for analysing plant cells in an efficient and reliable manner within a plant breeding and/or seed production process. Further, the analysis should allow standardization within a specific process and applicable at various locations, being it at the same research/production sites (greenhouse, open field, laboratory) or in different geographical regions, as seed manufacturers are usually operating globally.

This problem of the high complexity of plant cell analysis for the processes described above is solved according to the invention by a method for the determination of pollen viability and/or maturation grade of a pollen population, comprising mechanically removing immature or mature pollen grains from flowers; re-suspending pollen grains in an electrically conductive, specific and well-defined buffer for keeping the plant cells to remain viable; passing the pollen suspension through an appropriate filter with a pore size suitable for a microfluidic device being adapted to perform impedance flow cytometry (IFC); passing the filtered suspension through the microfluidic device calibrated for the respective pollen type and measuring the impedance of the pollen grains at predetermined frequencies; storing the measured impedance values of each pollen with the amplitude value and its correlated phase angle as well as the measurement frequencies; counting the pollen grains in the filtered suspension; and discriminating the pollen grains according to the amplitude and/or phase values by manually or automatically setting an appropriate gate and determining the viability ratio or maturation grade of the analysed pollen population.

The invention also relates to a use of a microfluidic device comprising at least one specific microfluidic chip and being adapted to perform impedance flow cytometry (IFC) with an alternate current (AC) field with frequencies in the range between 0.1 to 600 MHz, preferably from 0.1 to 200 MHz, most preferably from 0.25 to 30 MHz, during the selection of plant breeding material for male fertility/sterility, heat-, salt-, and/or stress-tolerance, during seed production processes, to control plant cell production processes, or to detect bacterial, fungal or other contaminations in plant production processes by identifying whether the plant cells are viable (alive) or non-viable (dead) and/or identifying plant cells as belonging to a specific development stage, respectively.

The current invention describes the resuspension of harvested pollen grains in an electrically conductive, specific and well-defined buffer for keeping the plant cells to remain viable and the use of radiofrequency impedance analysis for on-site pollen quality determination and its integration into the plant breeding and seed production processes of relevant vegetable and fruit plants. A conductive, specific and well-defined buffer must have the capability to keep the cells alive during the preparation and measurement as well as to provide sufficient conductivity for the measurement by using radiofrequency impedance analyses. Thus, the buffer must be adapted to the cell types of the analysed species.

By this method it is not only possible to easily differentiate between viable and dead pollen cells on-site, but also to distinguish different developmental stages of developing pollen in a highly efficient way. This analytical method can be applied during plant breeding processes as well as seed production and will contribute to plant breeding by selecting male sterile lines, improving doubled haploid production by health analysis via monitoring pollen viability, and optimising F1 hybrid seed production by pollen analysis of both parental lines. Furthermore, this method can be applied to select breeding lines under stress conditions, and help to control the quality of pollen that is used for germplasm conservation. This method can also be applied during plant development to control the fitness of the plant to adjust the optimal growth conditions for either fruit or seed production. Next to the analysis of the pollen viability the described technique also allows the detection of plant pathogens and their viability providing a new monitoring system for plant pathogens. Because of the cellular differences to plants cells, cells of plant pathogens have different impedance values. Impedance analysis of single cells can be generally applied to all plant species and is not restricted to the species described in this invention.

Specifically, the present invention is based on the fact that cells of any origin are surrounded by cellular membranes and/or cell walls, and that this cell membranes and/or cell walls exhibits specific capacities when exposed to an electric field. These capacities can be measured giving values of capacitance that reflect the physiological state of the cellular membrane, cell wall, and cytoplasm.

In the present invention plant cell capacitance is analysed by an impedance flow cytometer. Conventional Coulter counters measure the impedance using direct current (DC) or low frequency alternate current (AC, max. 1 kHz), allowing for reliable cell counting and cell size discrimination. EP 1 335 198 B1 discloses a micro fluidic approach with an electrode arrangement that permits impedance analysis of cells over a broad frequency range (100 kHz-20 MHz). High frequency analyses go beyond simple cell counting and sizing and interrogate the dielectric properties of cells, which allow for cell discrimination in various applications, such as cell differentiation, or animal, fungal, and bacterial cell viability, respectively (Schade-Kampmann et al., titled: ON-CHIP NON-INVASIVE AND LABEL-FREE CELL DISCRIMINATION BY IMPEDANCE SPECTROSCOPY, Cell Prolif. (2008), 41(5), p. 830-840). In contrast to conventional Coulter counter measurements, in which the signal amplitude is used for counting and sizing cells, high-frequency analyses provide information about the cell membrane capacitance and the cytoplasmic conductivity, which are important indicators of the physiological state of the cells. Impedance analysis on single cells in a frequency range up to 0.1 MHz allows splitting the amplitude and phase angle components and permits the discrimination of cells from non-cellular particles as well as discrimination of live/dead cells (Conrad et al., titled: IMPEDIMETRIC AND OPTICAL INTERROGATION OF SINGLE CELLS IN A MICROFLUIDIC DEVICE FOR REAL-TIME VIABILITY AND CHEMICAL RESPONSE ASSESSMENT, Biosensors and Bioelectronics (2008), 23, 845-851). The device used by Conrad et al. for this analysis, however, is trapping single cells prior to measuring the impedance signal and is therefore not suitable for the quick analysis of thousands of cells in a short time, which provides a reasonable base for statistical analyses.

The suitability or applicability of the method depends on the plant cell size, cell type, analysis buffer, and impedance flow cytometer. The microfluidic device has to be calibrated for the respective pollen type with regards to its channel width through which the pollen grains in the suspension move, and the used buffer.

The present invention provides a method that allows viability analysis that is independent of staining technologies, the analysis is reproducible and reliable, it does not require very specific equipment, can be applied at any location, and can be performed by any person after a short training period.

With "viability" herein is meant that a cell or organism is physiologically active. Physiologically active means that this cell or organism is able to divide, propagate, germinate, fuse or melt with another cell and/or to develop further.

The analysed plant cell can be surrounded by a plant cell wall, a membrane, or exine. This cell wall, membrane or exine encloses the typical cellular content of plants comprising the cytoplasm, one or more vacuoles, one or more nuclei, plastids, endoplasmic reticulum, Golgi apparatus, etc.

A plant cell with an exine is a plant cell which is a very specific type of cell wall. Plant cell with exine are called pollen grains and they belong to the class of reproductive plant cells deriving from a mature plant. Reproductive plant cells develop via different developmental steps into egg cells or pollen grains.

Pollen, the plant equivalent of the mammalian sperm cell, which is also known as germ cell or spore, is essential for the sexual reproduction of all plant species. Pollen develops within the anther of a floral bud from a microsporocyte via two cell divisions, a dyad (two diploid cells) and tetrad (four haploid cells form), into haploid unripe pollen grains or microspores. After release from the tetrad microspores develop via distinct stages into mature pollen grains that can be used for pollination.

Only species-related, healthy and viable pollen that got into contact with the stigma will germinate and form a pollen tube towards the plant egg cell (ovule) which is fertilized upon entry of the tip of the pollen tube into the microphylla. After the double fertilisation, endosperm (equivalent to the mammalian placenta) and zygotic embryos will form and mature within the seed coat. The majority of pollen grains have a haploid nuclear content (one set of chromosomes) but it can be also diploid (two sets of chromosomes) or poly- or aneuploid.

"Mature plant" herein means a plant, which has reached an advanced stage of development such that the plant produces at least one reproductive organ, preferably more of such organs, wherein from such reproductive organ viable progeny can be obtained. Such a reproductive organ can be a sexual reproductive organ, such as a flower, or vegetative reproductive organ, such as a tuber, stolon, rhizome, corm, bulbil or a bulb.

Herein a flower can be unisexual, i.e. having either at least a male reproductive organ (androecium) or at least a female reproductive organ (gynoecium); or herein a flower can be bisexual, i.e. having at least one male reproductive organ and at least one female reproductive organ.

A flower herein can be fertile or sterile. In case of a fertile flower, such a flower bears functional pollen and one or more functional egg cells, which can subsequently give rise to viable progeny. A flower with functional pollen and one or more functional egg-cells can produce one or more seeds by self-fertilization but also by cross-fertilization. In case of a sterile flower, such a flower does not produce seed(s) by self-fertilization due to the absence of any pollen or presence of non-functional pollen, respectively, but can produce seed (s) by cross-fertilization. Such a flower can be male-sterile or female-sterile. A male sterile flower, however, can be fertilized by functional pollen from another flower. Pollen of a female-sterile flower can be used to fertilize another flower. The male sterility of such flower can be a result of cytoplasmic male sterility (CMS), sporophytic self-incompatibility, gametophytic self-incompatibility or any other sterility system. The above biological terms are used in their art-recognized meaning.

The term "plant cell" herein refers to any cell, which is derived from a plant or plant material, including algae. Also meant is a protoplast or any cell from a liquid suspension or the like. The term "plant material" herein refers to any explant, piece or cutting derived from any structure, tissue or organ from a plant. Plant material herein can also refer to any tissue or organ of a plant. Said plant tissue or organ from which said explant, piece or cutting is derived comprises a cotyledon, hypocotyl, epicotyl, seed, callus, leaf, root, shoot, flower, anther, pollen, ovule, egg cell, fruit, meristem, primordium, inflorescence, petiole, protoplast, sink tissue, source tissue, seedling, sink organ, source organ, tuber, zygotic embryo, somatic embryo or embryos deriving from doubled haploids of haploids. Also included in this respect are cell cultures such as single cell cultures, suspensions, androgenic culture, gynogenic cultures. In particular, the term plant material refers to flower- or flower bud-derived tissue, cells in culture, and ground embryo and seed tissues.

According to one embodiment of the invention the plant cells are exposed within a specific microfluidic chip in the impedance flow cytometer (IFC) to an alternate current (AC) field with frequencies in the range between 0.1-600 MHz, preferably from 0.25-30 MHz. With these parameters the required results can be obtained.

In detail, according to a specific embodiment of the invention, for identifying whether the plant cells are viable (alive) or non-viable (dead), the method comprises arranging the stored impedance values with the amplitude value and the phase angle value in an x-y-matrix; determining a gate between an array of values having a lower and a higher phase angle; counting the pollen grain impedance values in both clouds; calculating a ratio between the amount of pollen having an impedance value with a phase angle below that gate and the amount of pollen having an impedance value with a phase angle above that gate; comparing the ratio with a respective ratio of a database comprising data of respective pollen for determining whether the viability of the pollen is sufficient for a given certain purpose; and displaying the result for that analysed population.

According to another embodiment of the invention, the method further comprises identifying the maturation grade by determining the amplitude values and/or the angle values as a function of the measurement frequencies; comparing the amplitude values and/or the angle values with the respective values of a database comprising data of respective pollen; identifying the plant cells as belonging to a specific developmental stage; and displaying the result for that analysed population.

In another embodiment the analysed plant cells are separated according to their different impedance signals and used for downstream processes, such as for breeding, seed, and/or fruit production purposes.

In a further embodiment the result is used to control a plant cell production process, to detect the state of the cell culture as well as bacterial or other contaminations in a plant cell production process.

In another further embodiment the result is used for the selection of plant breeding material for male fertility/sterility, heat-, salt-, and/or stress-tolerance.

According to another preferable embodiment the result is used for the optimization of plant growth conditions (for example illumination and humidity parameters in a greenhouse) required to obtain pollen with maximal viability.

For special purposes it is advantageous to determine a trigger parameter, which is normally composed of one of the measured impedance components (real or imaginary parts, amplitude and phase angle) and its value (=trigger level), for the identification of the characteristic of the pollen so that the impedance is only measured from pollen having a defined characteristic.

Preferably, determining the viability or maturation grade of the analysed pollen population is performed in real-time.

Further, according to the invention a microfluidic device comprising at least one specific microfluidic chip and being adapted to perform impedance flow cytometry (IFC) with an alternate current (AC) field with frequencies in the range between 0.1 to 600 MHz, preferably from 0.1 to 200 MHz, most preferably from 0.25 to 30 MHz, is used during the selection of plant breeding material for male fertility/sterility, heat-, salt-, and/or stress-tolerance, during seed production processes, to control plant cell production processes, or to detect bacterial, fungal or other contaminations in plant production processes by identifying whether the plant cells are viable (alive) or non-viable (dead) and/or identifying plant cells as belonging to a specific development stage, respectively.

An advantage of the present invention is that a plant cell does not have to be stained for viability analysis, the method is non-invasive, non-destructive and a high number of cells can be analysed in a short time frame.

Another advantage of the present invention includes the possibility to follow developmental processes of plant cells and that it is applicable to all plant species. The plant cell can be of somatic or reproductive origin.

A further advantage of the present invention is that by analysing cells of a plant the physiological fitness or viability of a plant is indicated.

A further advantage of the present invention is that the device, which performs the analysis, can be used right next to the plant delivering direct results.

A further advantage of the present invention is that the device, which performs the analysis, can be optimised depending on the specifications of the various plants.

An important advantage of the present invention is that the analysis can be standardized and therefore applied at different locations, providing comparable and reproducible results by using buffers optimized for and a microfluidic device specifically calibrated on the respective pollen type. It is possible, that one buffer and one calibration can be used for several different pollen types.

Application of the method according to the invention leads to an efficient and reliable viability analysis of plant cells independent of the species.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed.

BRIEF DESCRIPTION OF THE DRAWINGS

Other objects, advantages, and novel features of the invention will become apparent from the following detailed description of the invention when considered in conjunction with the drawing figures, wherein.

DETAILED DESCRIPTION OF THE INVENTION

Figure 1:
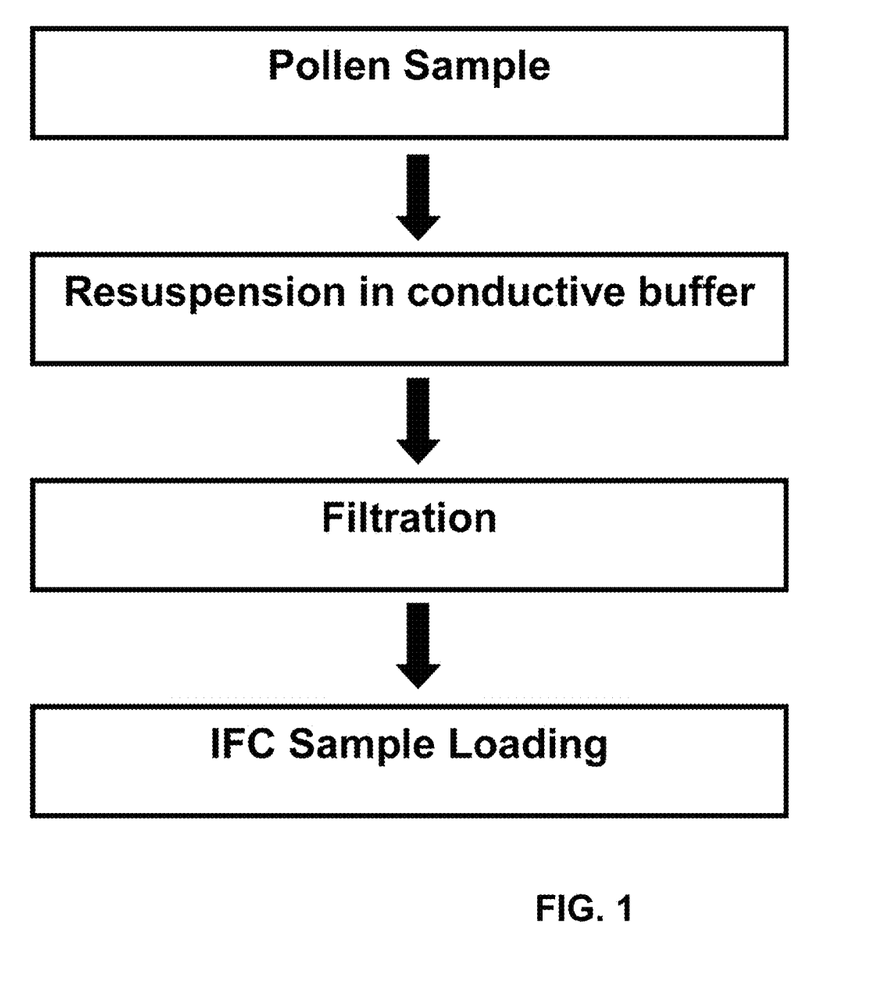
FIG. 1 illustrates a flow chart of sample preparation and loading procedure.

The method envisages that harvested pollen grains are re-suspended in liquid standard IFC buffers, filtered through sieves with appropriate mesh size and loaded onto the machine. FIG. 1 gives an example of the flow chart of sample preparation for IFC measurements. Standard IFC comprises any conductive and liquid buffer that allows the plant cells to remain viable.

Figure 2:
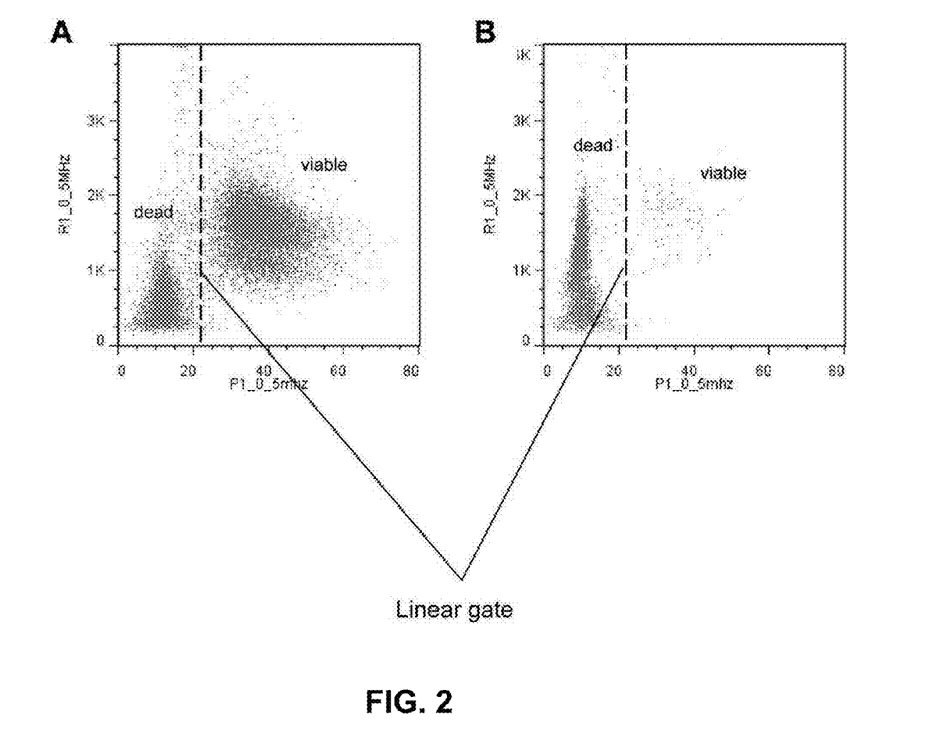
FIG. 2 demonstrates a separation of a non-viable and viable pollen population based on a different impedance phase signal.
Figure 3:
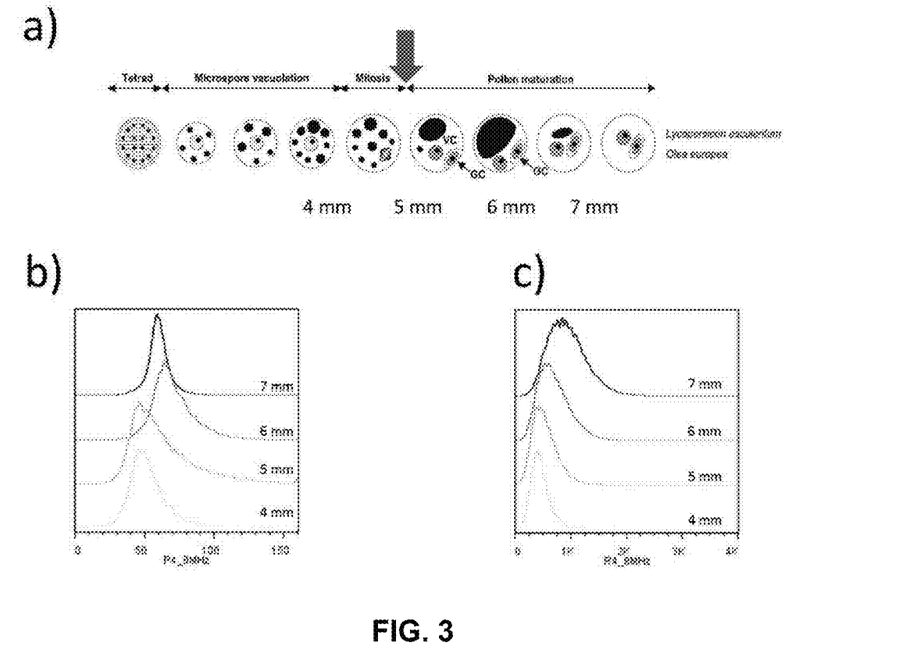
FIG. 3 demonstrates the discrimination of different developmental stages of pollen analysed by IFC with *Brassica* as an example.

After impedance measurement with the IFC the received values are stored according to the required result of the measurement in a respective format as shown in FIG. 2 and FIG. 3 for the following comparison with the respective data of the same plant species of a database.

The result either displays directly the measured values or only the outcome of the comparison with the database, e.g. only the information that the pollen are suitable for the defined purpose or not.

FIG. 2 shows two dot plots of a pollen viability analysis by IFC performed at 0.5 MHz. Plot A depicts the analysis of a typical fresh pollen sample of *Capsicum annuum* (pepper), containing both viable and non-viable pollen with each dot representing the impedance signal (x-axis=phase angle, y-axis=signal amplitude) of one pollen grain. To identify the dead pollen sub-population as those pollen grains with a lower phase angle value the same sample was heat-inactivated and analysed again. By setting an appropriate gate (linear, polygonal, etc.) it is easily possible to determine the ratio of viable pollen and thus to assess whether the harvested pollen sample is suitable for a subsequent pollination. Due to the clear separation of the dead and viable sub-population, the gate setting can also occur automatically without user intervention, simplifying the analysis process any further.

The determination of the pollen quality by IFC is reproducible and highly sensitive. For example, a significant correlation between expected and measured viabilities was obtained with defined mixtures of dead and viable pollen for both *Brassica oleracea* (cauliflower) and *Solanum lycopersicum* (tomato) pollen.

Impedance analysis of pollen cannot only be used for viability determination, but also for the differentiation of developmental stages. FIG. 3a shows a schematic representation of the various stages that a pollen grain encounters during its development. Changes in cell dimension and cell content (size of the vacuoles) can influence both the amplitude and phase angle of the impedance signal, respectively. This is demonstrated in FIG. 3b, where phase angle changes result from varying vacuole sizes, and in FIG. 3c, where the amplitudes change as a result of varying cell sizes. The analyses were performed with pollen grains of *Brassica oleracea* obtained from buds of the indicated sizes (4-7 mm).

Figure 4:
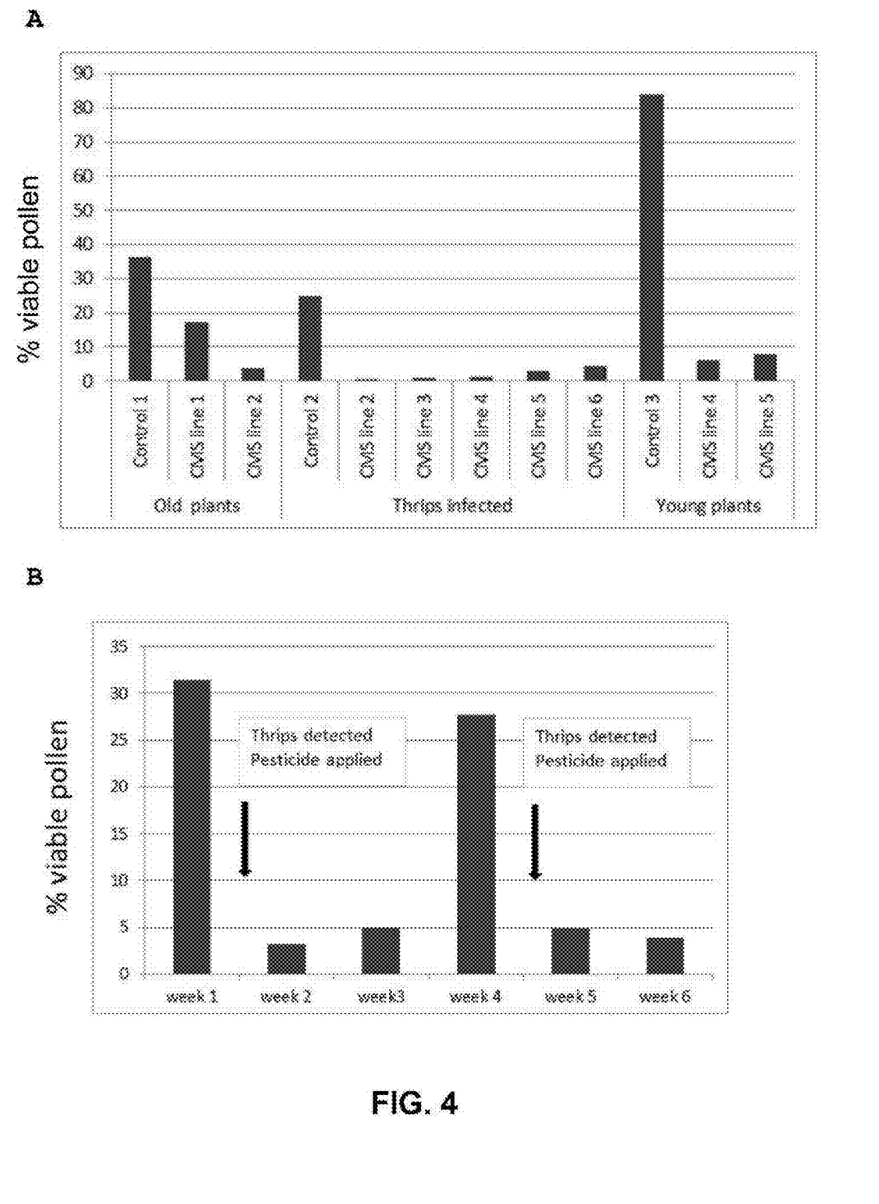
FIG. 4 demonstrates the suitability of IFC to select cytoplasmic male sterile lines, to detect the effect of pests or aging with *Raphanus* as an example, and to detect the effect of pesticide treatments on pollen viability with tomato as an example.

FIG. 4 illustrates the viability of pollen collected from *Raphanus* flower buds of cytoplasmic male sterile lines (CMS 1-6) along with a fully fertile line (Control 1-3). The analysis shows that younger plants (4 weeks, control 3) have a higher pollen viability than older plants (12 weeks, control 1 and 2), a phenomenon described by breeders but that has not been analysed before. Infection by pollen eating insects like Thrips that also affect the overall fitness of the plants plus application of pesticides ("old plants" and "Thrips-infected") also dramatically decrease pollen viability in both control and CMS lines.

Figure 5:
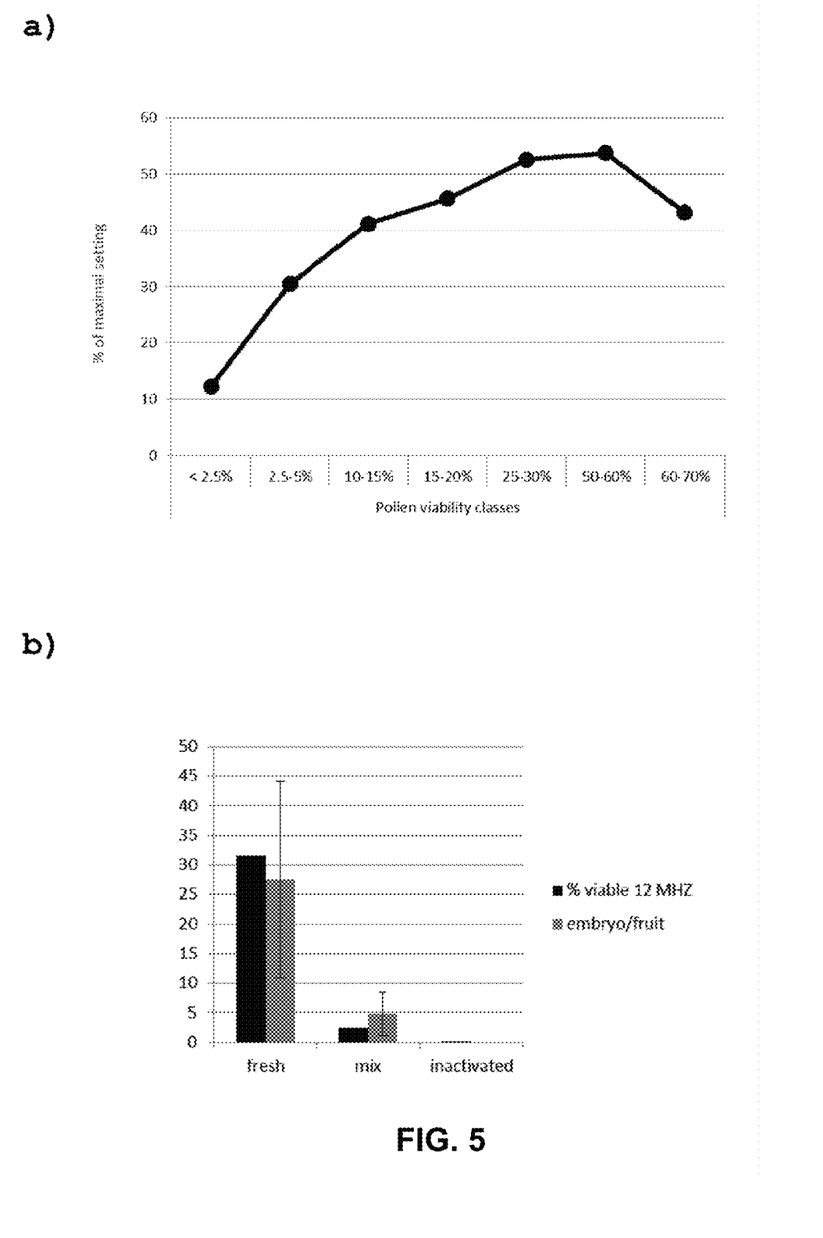
FIG. 5 illustrates a typical correlation between pollen viability determined by IFC and the resulting seed setting, which represents the relative amount of embryos per fruit, with tomato as an example.

FIGS. 5a and 5b show the correlation of pollen viability analysed by IFC at 12 MHz and the seed production. Tomato flowers were pollinated with different pollen qualities (% viable pollen) and the relative amount of viable seeds (seeds containing an embryo) was analysed to generate data of successful pollination (FIG. 5a). Flowers pollinated with a pollen viability higher than 25% show a seed setting above 50% of the maximal amount of seeds that can be obtained per fruit, as estimated by the number viable seeds obtained by natural selfing per fruit. Flowers pollinated with pollen of low viability, like less than 2.5%, successfully produce just 10-20% of the possible ovules. Pollen of very low viability or inactivated pollen lead to minimal amounts of seeds or to no seeds at all, respectively, as demonstrated in FIG. 5b. Only seeds that contain an embryo will give rise to a new plant.

Figure 6:
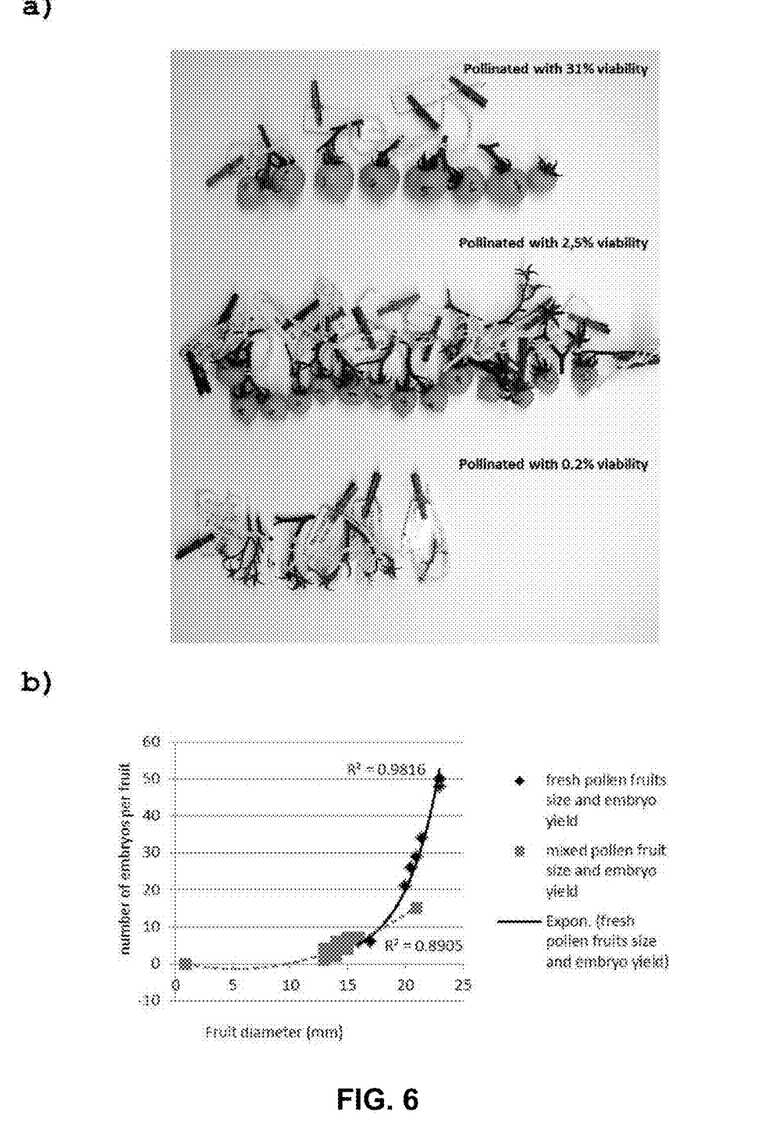
FIG. 6 visualizes the effect of the pollen quality (viability) used for pollination on the resulting fruit size with tomato as an example.

FIGS. 6a and 6b show the influence of pollen quality on fruit development. FIG. 6a shows an image of tomato fruits harvested 3 weeks after pollination prior to embryo analysis. The diameter of each harvested fruit was measured and the number of embryos per fruit was counted. Flowers that had been pollinated with the highest pollen quality (31%) had significantly bigger fruits and a higher number of embryo per fruits (FIG. 6a, upper row; 6b, black line) compared to a lower quality (FIG. 6a mid row; 6b, grey line). Flowers pollinated with a viablity of 0.2% did not produce any fruits and consequently no seeds. Thus, the use of IFC can also be an important tool during the fruit production process.

Figure 7:
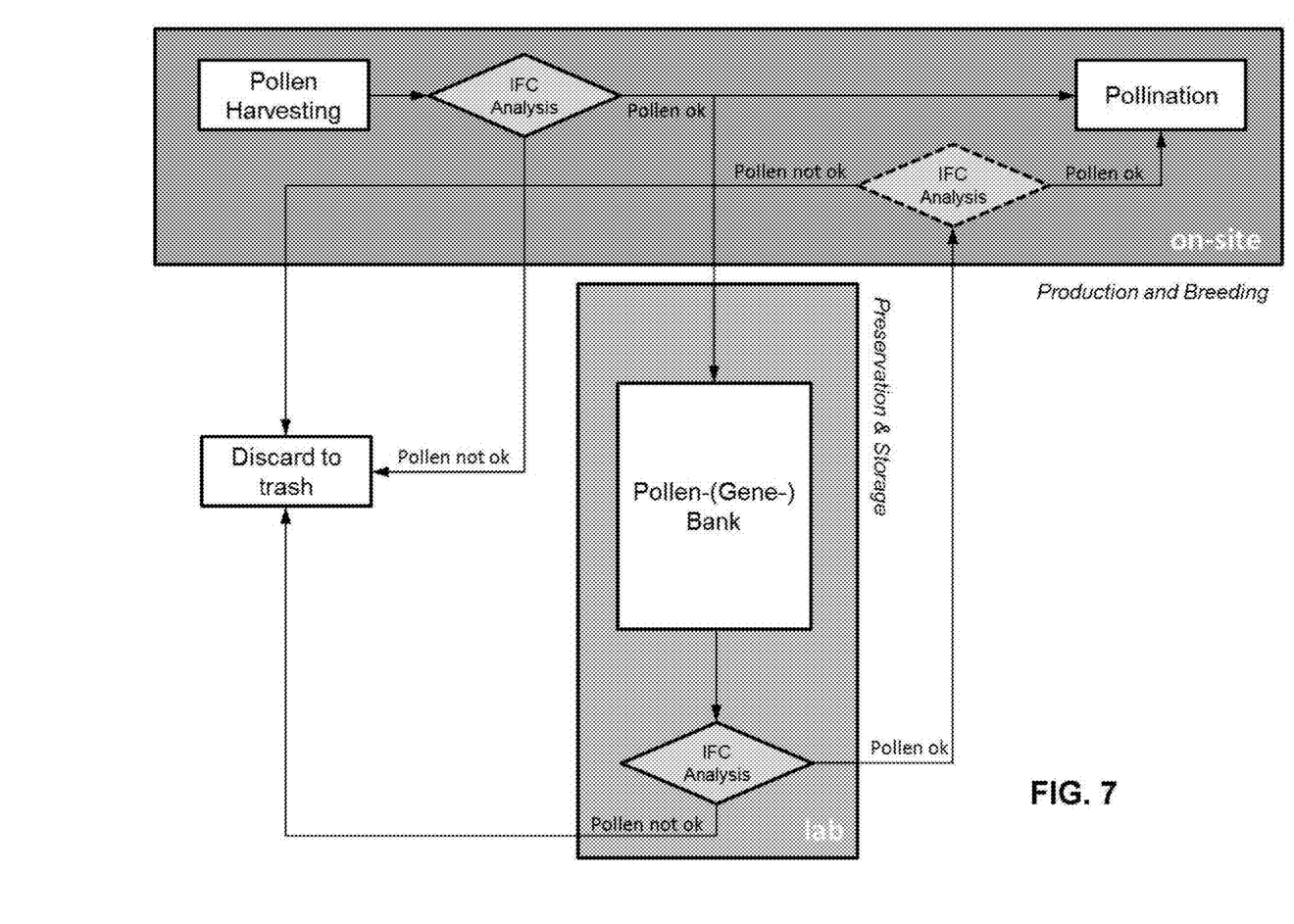
FIG. 7 illustrates the use of IFC during pollen processing for seed production or germplasm preservation.

FIG. 7 shows the principle and the application of the method for pollination and germplasm preservation purposes. The single steps are depicted in the block diagram. Impedance analysis of pollen can be performed in the greenhouse, field (=on-site) mainly for production process control or germplasm preservation programs, or in laboratory environment for further breeding or storage applications (pollen gene bank). The use of a standardized procedure allows a location- and operator-independent analysis and therefore leads to comparable results. This represents a massive improvement for seed manufacturers and breeders because pollen viability data can be tracked all over the various steps of the seed production or germplasm preservation process that often take place in geographically different locations. Thus, this pollen analysis method meets for the first time the requirements of globally acting seed manufacturers.

What is claimed is:

1. A method for determining at least one of pollen viability and maturation grade of a pollen population, comprising the steps:
    mechanically removing immature or mature pollen grains from flowers;
    re-suspending the pollen grains in an electrically conductive, specific and well-defined buffer for keeping the pollen grains to remain viable;
    passing a cell suspension with the pollen grains through a sieve with an appropriate mesh size suitable for a microfluidic device being adapted to perform impedance flow cytometry (IFC) by providing an alternate current (AC) field to form a filtered suspension;
    passing the filtered suspension through the microfluidic device calibrated for a respective pollen type and measuring an impedance of the pollen grains at predetermined frequencies;
    storing measured impedance values of each pollen grain with an amplitude value and its correlated phase angle as well as the predetermined frequencies;
    counting the pollen grains in the suspension; and
    discriminating the pollen grains according to the amplitude or phase values by manually or automatically setting an appropriate gate and determining a viable to non-viable ratio or maturation grade of the analysed pollen population.

2. The method according to claim 1, wherein the pollen grains are exposed within a specific microfluidic chip in an impedance flow cytometer (IFC) to an alternate current (AC) field with frequencies in a range between 0.1 to 600 MHz.

3. The method according to claim 1, further comprising the steps:
    identifying whether the pollen grains are viable (alive) or non-viable (dead) by arranging the stored impedance values with the amplitude value and the phase angle value in an x-y-matrix;
    determining a gate between data groups having a lower and a higher phase angle;
    counting the pollen grain impedance values of different data groups;
    calculating a ratio between the amount of pollen having an impedance value with a phase angle below the gate and the amount of pollen having an impedance value with a phase angle above the gate;
    comparing the ratio with a respective ratio of a database comprising data of respective pollen for determining whether the viability of the pollen is sufficient for a given certain purpose; and
    displaying the result for that analysed population.

4. The method according to claim 1, further comprising the steps:
    identifying the maturation grade by determining at least one of the amplitude values and the angle values as a function of the measurement frequencies;
    comparing the amplitude values and the angle values with the respective values of a database comprising data of respective pollen; and
    identifying the plant cells as belonging to a specific developmental stage; and
    displaying the result for that analysed population.

5. The method according to claim 1, wherein the analysed pollen grains are separated according to their different impedance signals and used for downstream processes and for breeding purposes.

6. The method according to claim 3, wherein the result is used for and during a seed production process, to control a plant cell production process, or to detect bacterial, fungal or other contaminations in these processes.

7. The method according to claim 3, wherein the result is used for the selection of plant breeding material for male fertility/sterility, heat-, salt-, and stress-tolerance.

8. The method according to claim 3, wherein the result is used for an optimization of plant growth conditions required to obtain pollen with maximal viability.

9. The method according to claim 1, further comprising determining a trigger parameter for an identification of a characteristic of the pollen.

10. The method according to claim 1, wherein determining the viability or maturation grade of the analysed pollen population is performed in real-time.

11. A method for determining at least one of pollen viability and maturation grade of a pollen population, comprising the steps:
- mechanically removing immature or mature pollen grains from flowers;
- re-suspending the pollen grains in an electrically conductive, specific and well-defined buffer for keeping the pollen grains to remain viable;
- passing a cell suspension with the pollen grains through a sieve with an appropriate mesh size suitable for a microfluidic device being adapted to perform impedance flow cytometry (IFC) by providing an alternate current (AC) field to form a filtered suspension;
- passing the filtered suspension through the microfluidic device calibrated for a respective pollen type and measuring an impedance of the pollen grains at predetermined frequencies;
- storing measured impedance values of each pollen grain with an amplitude value and its correlated phase angle as well as the predetermined frequencies;
- counting the pollen grains in the suspension;
- discriminating the pollen grains according to the amplitude or phase values by manually or automatically setting an appropriate gate and determining a viable to non-viable ratio or maturation grade of the analysed pollen population;
- identifying whether the pollen grains are viable (alive) or non-viable (dead) by arranging the stored impedance values with the amplitude value and the phase angle value in an x-y-matrix;
- determining a gate between data groups having a lower and a higher phase angle;
- counting the pollen grain impedance values of different data groups;
- calculating a ratio between the amount of pollen having an impedance value with a phase angle below the gate and the amount of pollen having an impedance value with a phase angle above the gate;
- comparing the ratio with a respective ratio of a database comprising data of respective pollen for determining whether the viability of the pollen is sufficient for a given certain purpose;
- displaying the result for that analysed population;
- identifying the maturation grade by determining at least one of the amplitude values and the angle values as a function of the measurement frequencies;
- comparing the amplitude values and the angle values with the respective values of a database comprising data of respective pollen; and
- identifying the plant cells as belonging to a specific developmental stage; and
- displaying the result for that analysed population.

* * * * *